United States Patent
Osypka et al.

(10) Patent No.: US 9,498,602 B2
(45) Date of Patent: Nov. 22, 2016

(54) GUIDED INTRAVASCULAR CATHETER SHEATH HAVING BI-DIRECTIONAL STEERING ASSEMBLY

(71) Applicant: Oscor Inc., Palm Harbor, FL (US)

(72) Inventors: Thomas P. Osypka, Palm Harbor, FL (US); Michael J. Gelineau, Lutz, FL (US); Brett Garlock, Palm Harbor, FL (US); Andrew J. Enerson, Hudson, FL (US)

(73) Assignee: Oscor Inc., Palm Harbor, FL (US)

( * ) Notice: Subject to any disclaimer, the term of this patent is extended or adjusted under 35 U.S.C. 154(b) by 28 days.

(21) Appl. No.: 14/715,728

(22) Filed: May 19, 2015

(65) Prior Publication Data

US 2015/0335861 A1    Nov. 26, 2015

Related U.S. Application Data

(60) Provisional application No. 62/000,720, filed on May 20, 2014.

(51) Int. Cl.
*A61M 25/01*  (2006.01)

(52) U.S. Cl.
CPC ..... *A61M 25/0147* (2013.01); *A61M 25/0136* (2013.01)

(58) Field of Classification Search
CPC ........... A61M 25/01; A61M 25/0105; A61M 25/0113; A61M 25/0136; A61M 25/01333; A61M 25/0147; A61M 25/0133; A61M 25/0144; A61M 2025/015
See application file for complete search history.

(56) References Cited

U.S. PATENT DOCUMENTS

| | | | |
|---|---|---|---|
| 4,730,616 A * | 3/1988 | Frisbie | A61M 25/01 604/164.02 |
| 5,395,329 A * | 3/1995 | Fleischhacker | A61M 25/0147 604/95.04 |
| 9,308,349 B2 * | 4/2016 | Rezac | A61M 25/0136 |
| 2006/0142694 A1 * | 6/2006 | Bednarek | A61M 25/0136 604/95.04 |
| 2012/0203169 A1 * | 8/2012 | Tegg | B29C 65/02 604/95.04 |
| 2015/0045696 A1 | 2/2015 | Osypka | |
| 2015/0057610 A1 | 2/2015 | Osypka et al. | |
| 2015/0057655 A1 | 2/2015 | Osypka | |
| 2015/0105721 A1 | 4/2015 | Osypka et al. | |

\* cited by examiner

*Primary Examiner* — Imani Hayman
*Assistant Examiner* — James D Ponton
(74) *Attorney, Agent, or Firm* — Locke Lord LLP; Scott D. Wofsy; Joshua L. Jones

(57) ABSTRACT

A steerable intravascular catheter is disclosed which includes an elongated sheath having a tubular body wall defining a central lumen and a deflectable distal end portion, a pair of laterally opposed elongated pull wires extending through the tubular body wall of the sheath and terminating within the distal end portion thereof, and a handle assembly having a longitudinal axis and operatively associated with a proximal end portion of the sheath, the handle assembly including an rotatable control knob for controlling bi-directional deflection of the distal end portion of the sheath, wherein bi-directional angular rotation of the control knob about the longitudinal axis of the handle assembly effectuates corresponding reciprocal axial movement of the laterally opposed pull wires in opposed axial directions and corresponding bi-directional deflection of the distal end portion of the sheath.

11 Claims, 6 Drawing Sheets

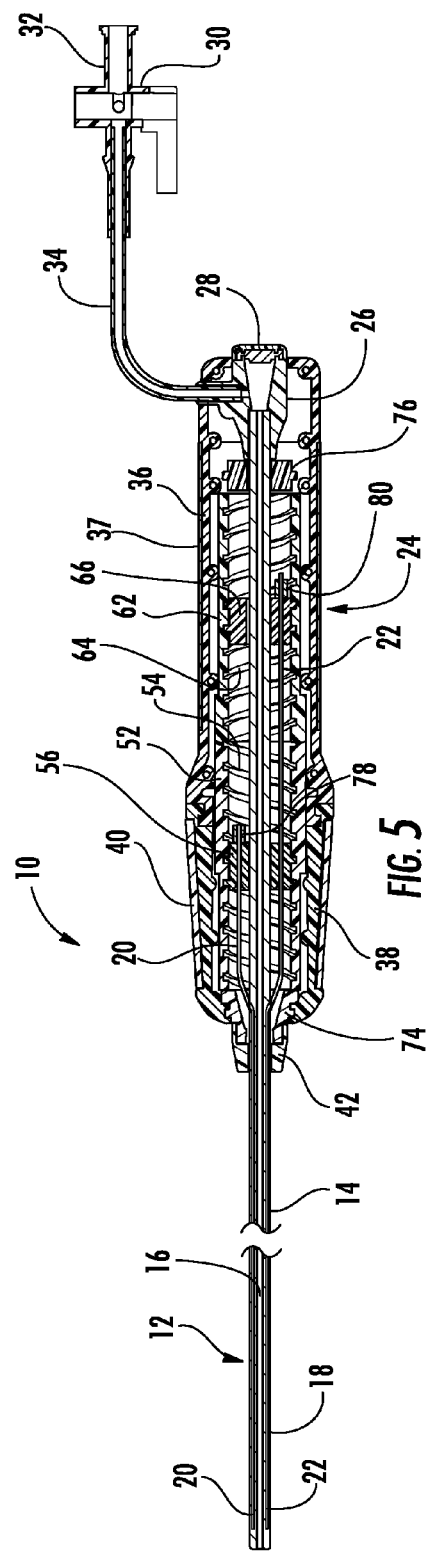

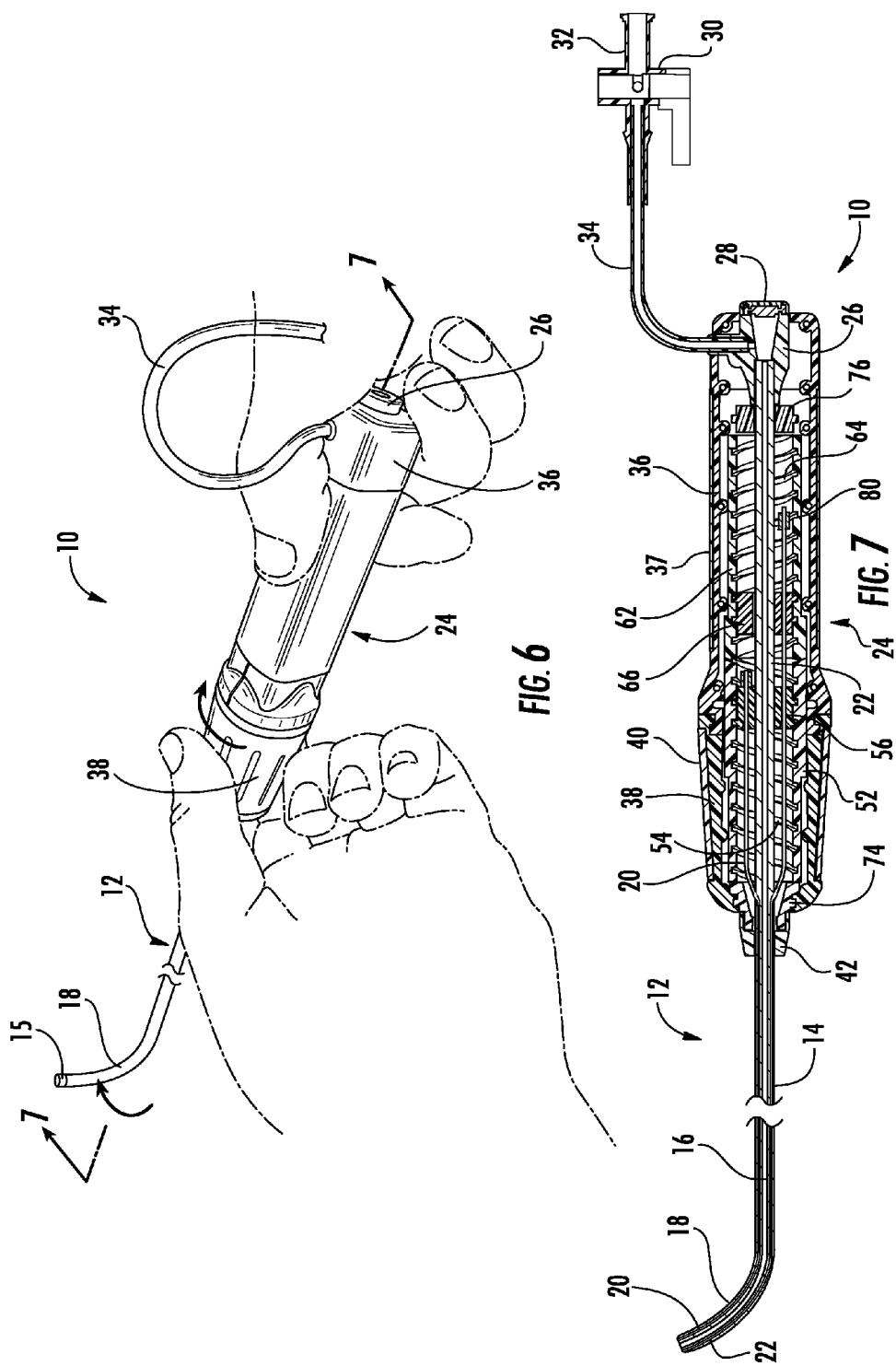

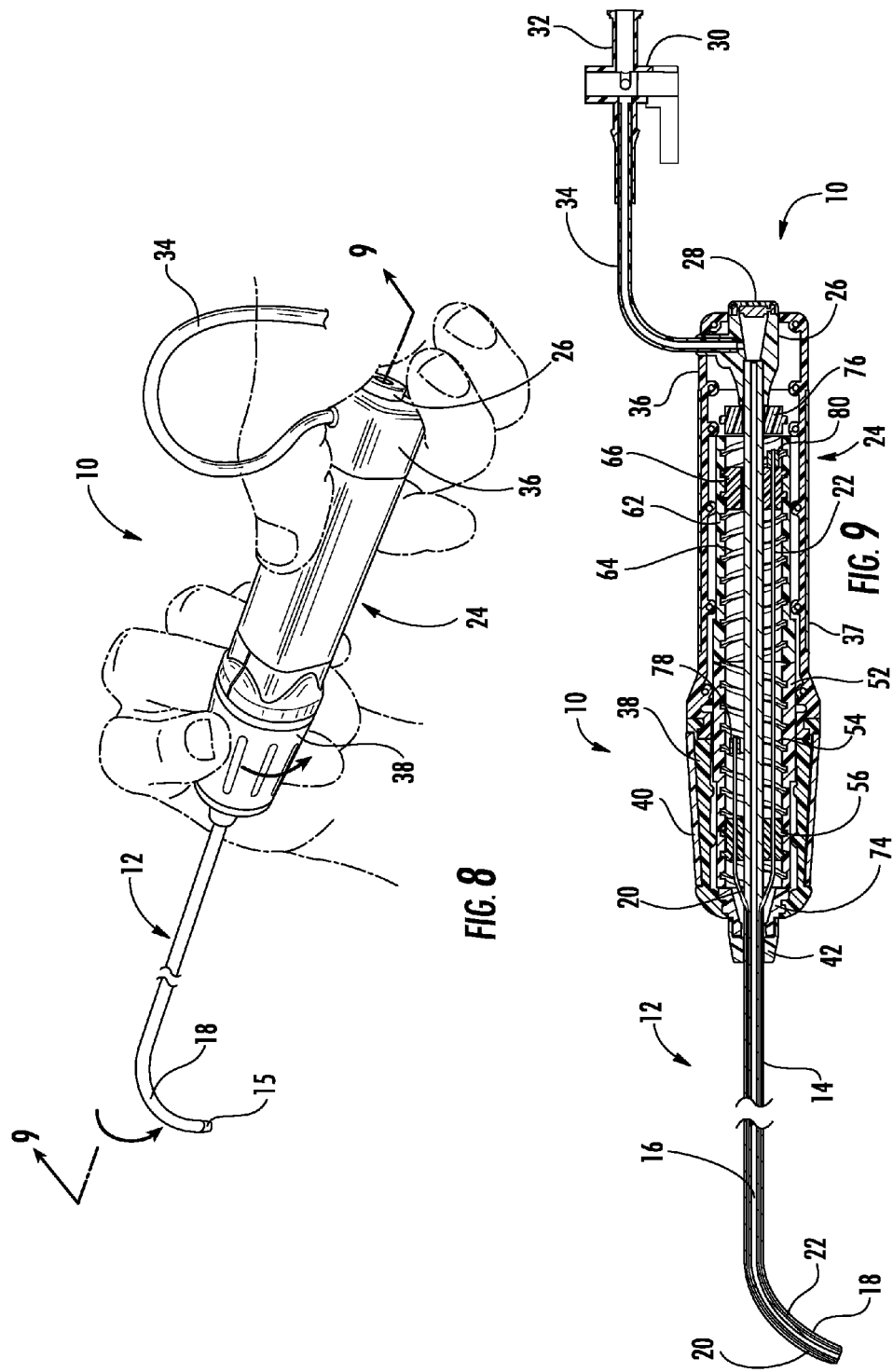

GUIDED INTRAVASCULAR CATHETER SHEATH HAVING BI-DIRECTIONAL STEERING ASSEMBLY

CROSS-REFERENCE TO RELATED APPLICATIONS

The subject application claims the benefit of priority to U.S. Provisional Patent Application Ser. No. 62/000,720, filed on May 20, 2014, the disclosure of which is herein incorporated by reference in its entirety.

BACKGROUND OF THE INVENTION

1. Field of the Invention

The subject invention relates to intravascular catheters, and more particularly, to a guided intravascular catheter sheath having a bi-directional steering assembly for accurately placing the distal end of the sheath at a targeted location in a patient's body, to facilitate the introduction of a diagnostic and/or therapeutic device to the targeted location.

2. Description of Related Art

There are many instances where physicians must introduce diagnostic and therapeutic devices into the body, such as diagnostic and therapeutic electrodes, ultrasound transducers and other surgical tools. The diagnostic and therapeutic devices are often carried by catheters, which allow physicians to gain access to the body in a minimally invasive manner by way of bodily lumens. In cardiac treatment, for example, a catheter is advanced through a main vein or artery into the region of the heart that is to be treated.

One method of introducing diagnostic and therapeutic devices into the body is to introduce a tubular member (typically a "sheath") into the vicinity of the targeted region. A diagnostic or therapeutic device is then passed through the sheath to the targeted region. If necessary, the diagnostic or therapeutic apparatus may be removed after its function is performed, but the sheath can be left in place, so that other devices can be advanced to the targeted region to complete the diagnostic and/or therapeutic procedure.

Precise placement of the diagnostic or therapeutic devices is very important, especially in those procedures concerning the heart. To that end, some conventional sheaths are guided to the targeted region with a steerable catheter that is located within the sheath lumen. Once the sheath reaches the targeted region, the steerable catheter is removed from the sheath and a catheter carrying the diagnostic or therapeutic device is advanced through the lumen. This type of sheath lacks any onboard steering mechanism. As a result, redeployment of the distal portion of sheath, even to a region in close proximity to the initially targeted region, requires the withdrawal of the diagnostic or therapeutic apparatus and the reintroduction of the steering catheter.

Other sheaths include a steering mechanism that allows the physician to guide the distal portion of the sheath to the targeted region. An example of a highly maneuverable bidirectional steerable sheath is disclosed in commonly assigned U.S. Patent Application Publication 2015/0057610 to Osypka et al. While this device is well suited for the precise placement of diagnostic or therapeutic devices within a patient's body, the bi-directional steering mechanism associated therewith is relatively complex, having several cooperating structural components that are relatively difficult to manufacture and assemble at a low cost. Accordingly, there remains a need in the art for a steerable sheath with a bi-directional steering mechanism that is less complex, easy to use and more easily manufactured and assembled.

SUMMARY OF THE INVENTION

The subject invention is directed to a new and useful guided intravascular catheter that includes a bi-directional steering mechanism that is easy to use and more easily manufactured and assembled than other devices known in the art. The catheter is adapted and configured to facilitate the introduction of diagnostic and therapeutic devices into the vasculature of a patient.

The steerable catheter of the subject invention includes an elongated sheath having a tubular body wall defining a central lumen and a deflectable distal end portion. A pair of laterally opposed elongated pull wires extend through the tubular body wall of the sheath and terminate within the distal end portion thereof. The catheter further includes a handle assembly having a longitudinal axis and operatively associated with a proximal end portion of the sheath. The proximal end portion of the sheath extends entirely through the handle assembly and terminates at a sealed access port communicating with the central lumen defined by the tubular body wall.

The handle assembly includes a rotatable control knob for controlling bi-directional deflection of the distal end portion of the sheath. Moreover, bi-directional angular rotation of the control knob about the longitudinal axis of the handle assembly effectuates corresponding reciprocal axial movement of the laterally opposed pull wires in opposed axial directions and corresponding bi-directional angular deflection of the distal end portion of the sheath.

The handle assembly includes a drive mechanism for actuating the laterally opposed elongated pull wires in response to the bi-directional angular rotation of the control knob. The drive mechanism includes a distal drive gear mounted for angular rotation about the longitudinal axis of the handle assembly, having a threaded bore and a cooperating threaded distal drive sleeve positioned within the threaded bore and supported for reciprocal axial movement therein. The drive mechanism also includes a proximal drive gear mounted for angular rotation about the longitudinal axis of the handle assembly, having a threaded bore and a cooperating threaded proximal drive sleeve positioned within the threaded bore and supported for reciprocal axial movement therein.

The proximal and distal drive gears have fixed axial positions relative to the longitudinal axis of the handle assembly, and they are interlocked end to end with one another. Preferably, the distal drive gear has a polygonal belt extending about the circumference thereof for engaging a complementary shaped recess formed in an interior wall of the control knob. The proximal and distal drive sleeves have fixed angular positions relative to the longitudinal axis of the handle assembly. Preferably, the threaded bore of the proximal drive gear has a first thread pitch and the threaded bore of the distal drive gear has a second thread pitch that runs in a direction opposite the first thread pitch.

The proximal and distal drive sleeves are supported for reciprocal axial movement on a pair of laterally opposed guide rods that are extend parallel to the longitudinal axis of the handle assembly. Preferably, a proximal end of one of the pull wires is anchored to the proximal drive sleeve and a proximal end of the other pull wire is anchored to the distal drive sleeve.

These and other features of the steerable intravascular catheter of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the steerable intravascular catheter of the subject invention appertains will readily understand how to make and use the device without undue experimentation, preferred embodiments thereof will be described in detail herein below with reference to certain figures, wherein:

FIG. 5 is a cross-sectional view of the steerable intravascular catheter of the subject invention, taken along line 4-4 of FIG. 1, with bi-directional steering mechanism disposed in a neutral position, wherein the distal end portion of the sheath is aligned with the longitudinal axis of the sheath;

FIG. 6 is an illustration showing the way in which the control knob of the handle assembly is rotated in a clockwise direction to cause the distal end portion of the sheath to deflect in a first direction;

FIG. 7 is a cross-sectional view of the steerable intravascular catheter of the subject invention, taken along line 7-7 of FIG. 6, showing the relative positions of the components of the bi-directional steering mechanism when the control knob is rotated as shown in FIG. 6;

FIG. 8 is an illustration showing the way in which the control knob of the handle assembly is rotated in a counter-clockwise direction to cause the distal end portion of the sheath to deflect in a second direction; and FIG. 9 is a cross-sectional view of the steerable intravascular catheter of the subject invention, taken along line 9-9 of FIG. 8, showing the relative positions of the components of the bi-directional steering mechanism when the control knob is rotated as shown in FIG. 8;

DETAILED DESCRIPTION OF THE PREFERRED EMBODIMENTS

Figure 1:
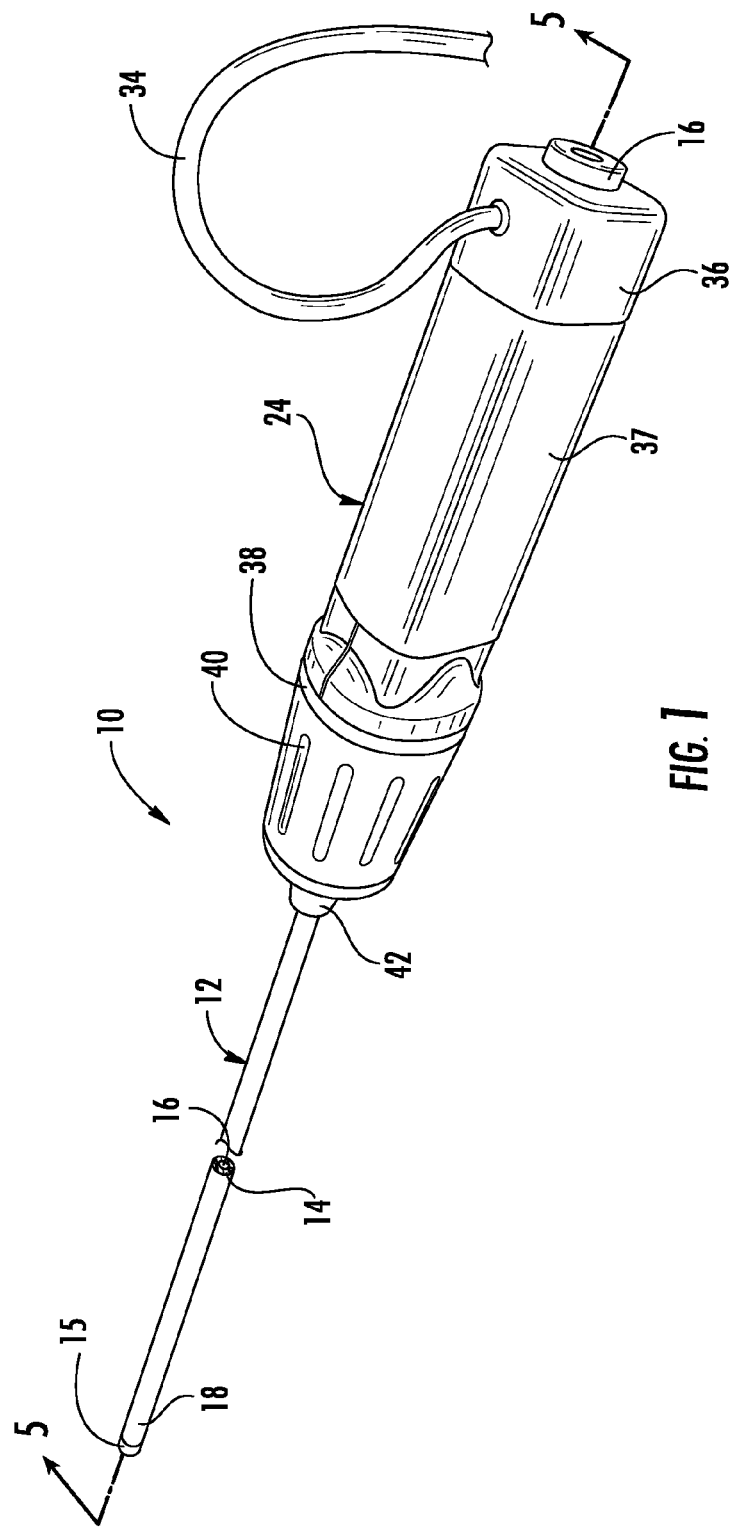
FIG. 1 is a perspective view of a steerable intravascular catheter device constructed in accordance with a preferred embodiment of the subject invention.

Referring now to the appended drawings, wherein like reference numerals identify similar structures or features of the subject invention, there is illustrated in FIG. 1 a new and useful steerable intravascular catheter constructed in accordance with a preferred embodiment of the subject invention and designated generally by reference numeral 10. Steerable intravascular catheter 10 is adapted and configured to facilitate the intracardiac, renal and/or peripheral placement of diagnostic and therapeutic devices during a surgical procedure.

Referring to FIG. 1, the steerable intravascular catheter 10 of the subject invention is intended for interventional use and/or transseptal use. It includes an elongated sheath 12 having a tubular body wall 14 defining a central lumen 16 to accommodate the introduction of diagnostic and/or therapeutic devices to the targeted procedure site. The sheath 12 is designed to be flexible and can have an inner lumen diameter ranging from about 6.5 F to about 8.5 F, and a usable length ranging from about 45 cm up to about 90 cm.

The sheath 12 is provided with a hydrophobic coating that enables smooth access to the vasculature of a patient. The tubular body wall 14 is preferably reinforced with a braided or woven material to provide enhanced control and resist kinking during use. The sheath 12 has a deflectable distal end portion 18 that promotes precise and reliable tip adjustment for fast access to difficult to reach sites. The tip 15 of the deflectable distal end portion 18 of sheath 12 is radiopaque to provide a surgeon with enhanced visibility, enabling accurate positioning during a procedure.

Referring briefly to FIG. 5, two pull wires 20 and 22 (upper and lower) extend through the tubular body wall 14 of sheath 12 on opposite sides of the central lumen 16. The pull wires 20 and 22 terminate within the deflectable distal end portion 18 of sheath 12. As explained in more detail below, pull wires 20 and 22 facilitate the remotely controlled bi-directional deflection of the distal end portion 18 of sheath 12 during an intravascular procedure. The total amount of tip deflection, as measured across the inside of the deflected curve, will vary depending upon the intended use of the catheter. For example, in a catheter designed for interventional use, the total amount of tip deflection can range from 9 mm up to about 17 mm. Whereas, in a catheter designed for transseptal use, the total amount of tip deflection can range from 17 mm up to about 50 mm.

Figure 2:
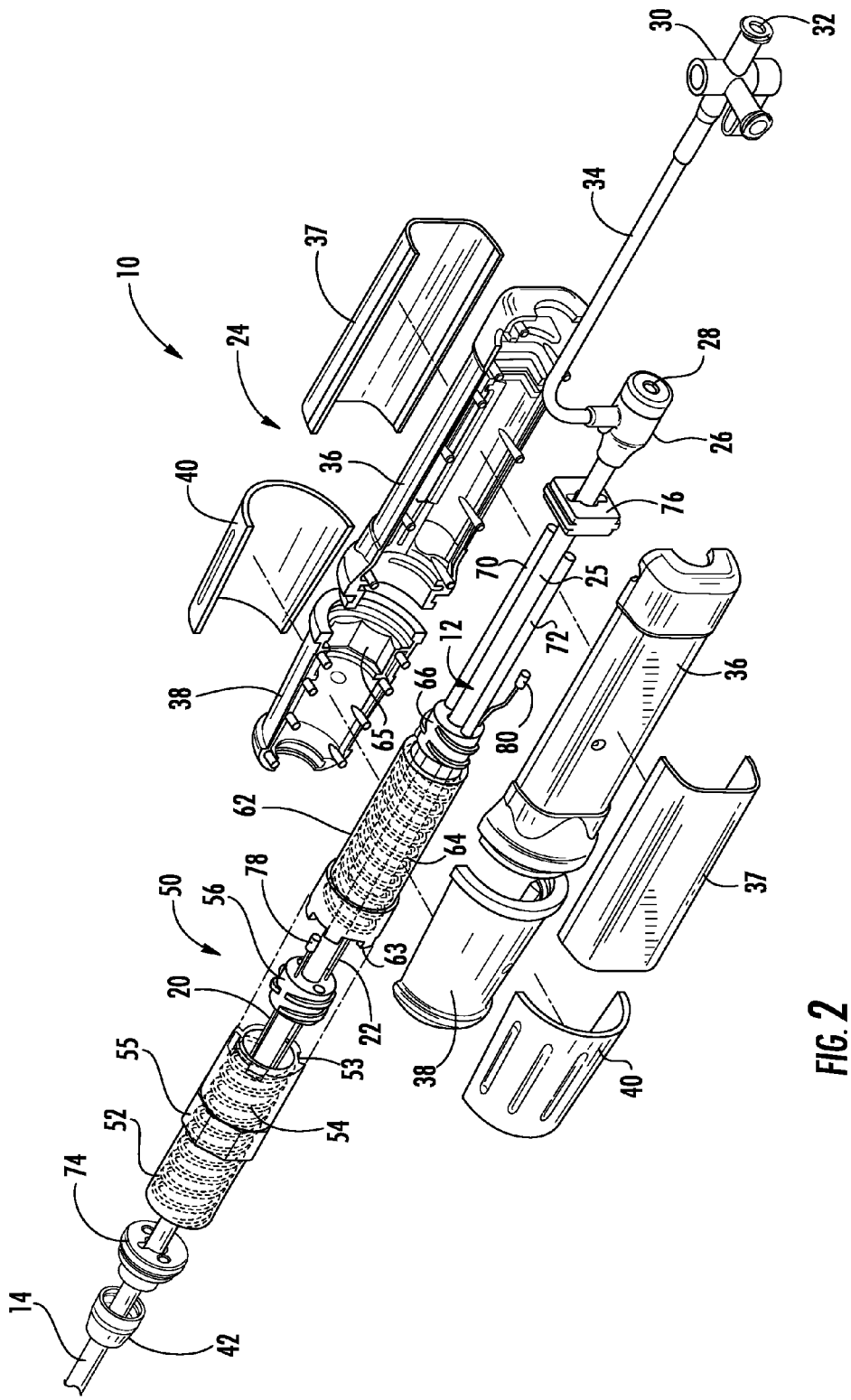
FIG. 2 is an exploded perspective view of the handle assembly of the steerable intravascular catheter device shown in FIG. 1, with the component parts of the steering mechanism separated for ease of illustration.

Referring now to FIG. 2, the steerable intravascular catheter 10 of the subject invention further includes an ergonomically shaped elongated handle assembly 24, which has a longitudinal axis extending therethrough and is operatively associated with a proximal end portion 25 of the sheath 12. More particularly, the proximal end portion 25 of sheath 12 extends entirely through the handle assembly 24 and it terminates at a sealed access port 26. The access port 26 communicates with the central lumen 16 defined by the tubular body wall 14, and it includes a hemostatic valve 28 designed to minimize blood loss and prevent air embolisms. A flush port 30 with standard leur fittings 32 communicates with access port 26 by way of a flexible tube 34.

The handle assembly 24 is made of an injection molded plastic material and constructed in a bifurcated manner. It includes a main body portion 36 and a rotatable deflection control knob 38 with a conical nose piece 42. The main body portion 36 has a rubberized outer shell 37 and deflection control knob 36 has a ribbed outer shell 40 to enhance tactile control of the catheter. The control knob 38 is adapted and configured to effectuate bi-directional deflection of the distal end portion 18 of the sheath 12. Moreover, bi-directional angular rotation of the control knob 38 about the longitudinal axis of the handle assembly 24 (i.e., clockwise and counter-clockwise rotation) effectuates corresponding reciprocal axial movement of the two pull wires 20 and 22 in opposed axial directions. This in turn causes the corresponding bi-directional angular deflection of the distal end portion 18 of sheath 12, as discussed in more detail below, with reference to FIGS. 6 through 8.

With continuing reference to FIG. 2, handle assembly 24 includes an internal drive mechanism designated generally by reference numeral 50 for actuating the elongated pull wires 20 and 22 in response to the bi-directional angular rotation of the control knob 38. The drive mechanism 50 includes a generally cylindrical distal drive gear 52 mounted for angular rotation about the longitudinal axis of the handle assembly 24. The distal drive gear 52 has a threaded internal bore 54. A cooperating threaded distal drive sleeve 56 is positioned within the threaded internal bore 54 and is supported for reciprocal axial movement therein.

The drive mechanism 50 also includes a generally cylindrical proximal drive gear 62 that is also mounted for angular rotation about the longitudinal axis of the handle assembly 24. The proximal drive gear 62 has a threaded internal bore 64 and a cooperating threaded proximal drive sleeve 66 positioned therein and supported for reciprocal axial movement.

The distal and proximal drive gears 52 and 62 have fixed axial positions relative to the longitudinal axis of the handle assembly 24. The two drive gears 52 and 62 are interlocked end to end with one another by way of cooperating structural features 53 and 63. The distal drive gear 52 has a polygonal belt 55 extending about the circumference thereof for engaging a complementary shaped recess 65 formed in an interior wall of the control knob 38. Consequently, when deflection control knob 38 is rotated about the axis of the handle assembly 24, the interlocked drive gears 52 and 62 will rotate therewith to steer the deflectable distal end portion 18 of sheath 12.

The pitch of the threaded bore 54 of the distal drive gear 52 runs in a direction that is opposite the direction of the pitch of the threaded bore 64 of proximal drive gear 62. However, the pitch angles of both threaded bores are the same. Consequently, when the interlocked drive gears 52 and 62 rotate together about the longitudinal axis of handle assembly 24, the drive two sleeves 56 and 66 will move simultaneously toward and away from one another along the longitudinal axis of the handle assembly 24, as illustrated for example in FIGS. 7 and 9.

Figure 3:
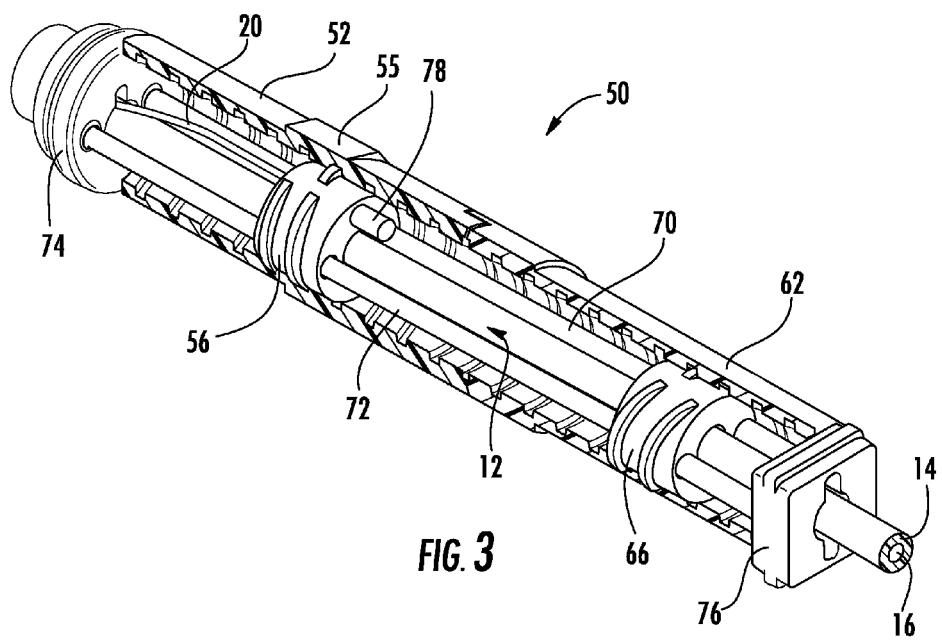
FIG. 3 is a perspective view, in partial cross-section, of the steering mechanism housed within the handle assembly of the intravascular catheter of FIG. 1, as viewed from above.
Figure 4:
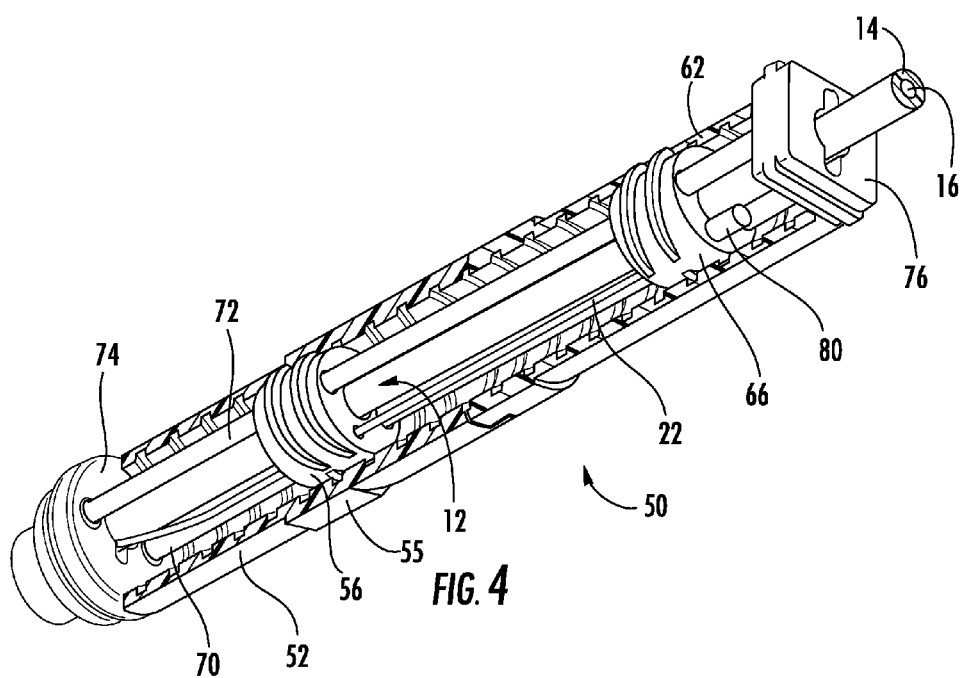
FIG. 4 is a perspective view, in partial cross-section, of the steering mechanism housed within the handle assembly of the intravascular catheter of FIG. 1, as viewed from below.

Referring now to FIGS. 3 and 4, the proximal and distal drive sleeves 56 and 66 have fixed angular positions relative to the longitudinal axis of the handle assembly 24. More particularly, the distal and proximal drive sleeves 56 and 66 are supported for reciprocal axial movement on a pair of laterally opposed PTFE coated guide rods 70 and 72 that extend parallel to the longitudinal axis of the handle assembly 24. The guide rods 70 and 72 are supported within handle assembly 24 by and between a circular distal support member 74 and a square proximal support member 76. The distal and proximal support members 74 and 76 both have a central aperture for accommodating the passage of the proximal end portion 25 of sheath 12.

With continuing reference to FIGS. 3 and 4, the proximal end of pull wire 20 is anchored to the distal drive sleeve 56 by a distal anchor 78, so that when the distal sleeve 56 translates in a proximal direction, the pull wire 22 will be drawn with it, causing the distal end portion 18 of sheath 12 to deflect in a first direction. Similarly, the proximal end of pull wire 22 is anchored to the proximal drive sleeve 66 by a proximal anchor 80, so that when the proximal sleeve 66 translates in a proximal direction pull wire 22 will be drawn with it, causing the distal end portion 18 of sheath 12 to deflect in a second opposite direction.

Referring now to FIG. 5, when the elongated sheath 12 is in a straightened orientation, so that the central lumen 16 is aligned with the longitudinal axis of the handle assembly 24, the two drive sleeves 56 and 66 are located in a neutral position relative to the two respective drive gears 52 and 62. That is, distal drive sleeve 56 is positioned generally in the middle of the internal bore 54 of the distal drive gear 52 and proximal drive sleeve 66 is positioned generally in the middle of the internal bore 64 of the proximal drive gear 62, as shown in FIG. 5.

In use, when the control knob 38 is angularly rotated in a clockwise direction, as illustrated in FIG. 6, the two interlocked drive gears 52 and 62 will rotate in a clockwise direction, causing the two drive sleeves 56 and 66 to move toward one another within their respective drive gears 52 and 62. Consequently, the pull wire 20 anchored to the distal drive sleeve 56 will be drawn in a proximal direction (rearwardly), while pull wire 22 will remain stationary, unaffected by the distal (forward) movement of the proximal drive sleeve 66, as illustrated in FIG. 7. This movement of pull wire 20 will result in the angular deflection of the distal end portion 18 of sheath 12 in a first direction, as shown.

Conversely, when the control knob 38 is angularly rotated in a counter-clockwise direction, as illustrated in FIG. 8, the two interlocked drive gears 52 and 62 will rotate in a counter-clockwise direction, causing the two drive sleeves 56 and 66 to move away from each other within their respective drive gears 52 and 62. Consequently, the pull wire 22 anchored to the proximal drive sleeve 66 will be drawn proximally (rearwardly), while pull wire 20 will remain stationary, unaffected by the distal (forward) movement of the distal drive sleeve 56. This movement of pull wire 22 will result in the angular deflection of the distal end portion 18 of sheath 12 in a second direction, as shown.

While the steerable intravascular catheter of the subject invention has been shown and described with reference to preferred embodiments, those skilled in the art will readily appreciate that various changes and/or modifications may be made thereto without departing from the spirit and scope of the subject invention as defined by the appended claims.

What is claimed is:

1. A steerable intravascular catheter, comprising:
   a) an elongated sheath having a tubular body wall defining a central lumen and a deflectable distal end portion;
   b) a pair of laterally opposed elongated pull wires extending through the tubular body wall of the sheath and terminating within the distal end portion thereof;
   c) a handle assembly having a longitudinal axis and operatively associated with a proximal end portion of the sheath, the handle assembly including a rotatable control knob for controlling bi-directional deflection of the distal end portion of the sheath, wherein bi-directional angular rotation of the control knob about the longitudinal axis of the handle assembly effectuates corresponding reciprocal axial movement of the laterally opposed pull wires in opposed axial directions and corresponding bi-directional angular deflection of the distal end portion of the sheath; and
   d) a drive mechanism associated with the handle assembly for actuating the laterally opposed elongated pull wires in response to the bi-directional angular rotation of the control knob, the drive mechanism having a distal drive gear mounted for angular rotation about the longitudinal axis of the handle assembly, the distal drive gear having a threaded bore and a cooperating threaded distal drive sleeve positioned within the threaded bore of the distal drive gear and supported for reciprocal axial movement therein, the drive mechanism further having a proximal drive gear mounted for angular rotation about the longitudinal axis of the handle assembly, the proximal drive gear having a threaded bore and a cooperating threaded proximal drive sleeve positioned within the threaded bore of the proximal drive gear and supported for reciprocal axial movement therein, wherein the proximal and distal drive gears have fixed axial positions relative to the longitudinal axis of the handle assembly and the proximal and distal drive sleeves have fixed angular positions relative to the longitudinal axis of the handle assembly, and wherein the proximal and distal drive sleeves are supported for reciprocal axial movement along a pair of laterally opposed cylindrical guide rods that extend parallel to the longitudinal axis of the handle assembly through corresponding circular apertures formed in each of the proximal and distal drive sleeves.

2. A steerable intravascular catheter as recited in claim 1, wherein the proximal and distal drive gears are interlocked end to end with one another.

3. A steerable intravascular catheter as recited in claim 2, wherein the distal drive gear has a polygonal belt extending about the circumference thereof for engaging a complementary shaped recess formed in an interior wall of the control knob.

4. A steerable intravascular catheter as recited in claim 1, wherein the threaded bore of the proximal drive gear has a first thread pitch and the threaded bore of the distal drive gear has a second thread pitch that runs in a direction opposite the first thread pitch.

5. A steerable intravascular catheter as recited in claim 1, wherein a proximal end of one of the pull wires is anchored to the proximal drive sleeve and a proximal end of the other pull wire is anchored to the distal drive sleeve.

6. A steerable intravascular catheter as recited in claim 1, wherein the proximal end portion of the sheath extends entirely through the handle assembly and terminates at a sealed access port communicating with the central lumen defined by the tubular body.

7. A steerable intravascular catheter, comprising:
   a) an elongated sheath having a tubular body wall defining a central lumen and a deflectable distal end portion;
   b) a pair of laterally opposed elongated pull wires extending through the tubular body wall of the sheath and terminating within the distal end portion thereof;
   c) a handle assembly having a longitudinal axis and operatively associated with a proximal end portion of the sheath, the handle assembly including a control knob configured for bi-directional angular rotation about the longitudinal axis of the handle assembly to control bi-directional angular deflection of the distal end portion of the sheath; and
   d) a drive mechanism housed within the handle assembly for actuating the laterally opposed elongated pull wires in response to the bi-directional angular rotation of the control knob, the drive mechanism including a distal drive gear mounted for angular rotation about the longitudinal axis of the handle assembly, the distal drive gear having a threaded bore and a cooperating threaded distal drive sleeve positioned within the threaded bore of the distal drive gear and supported for reciprocal axial movement therein, the drive mechanism further including a proximal drive gear mounted for angular rotation about the longitudinal axis of the handle assembly, the proximal drive gear having a threaded bore and a cooperating threaded proximal drive sleeve positioned within the threaded bore of the proximal drive gear and supported for reciprocal axial movement therein, wherein the proximal and distal drive sleeves are supported for reciprocal axial movement on a pair of laterally opposed cylindrical guide rods that extend parallel to the longitudinal axis of the handle assembly through corresponding circular apertures formed in each of the proximal and distal drive sleeves.

8. A steerable intravascular catheter as recited in claim 7, wherein the proximal and distal drive gears are interlocked end to end with one another, and the distal drive gear has a polygonal belt extending about the circumference thereof for engaging a complementary shaped recess formed in an interior wall of the control knob.

9. A steerable intravascular catheter as recited in claim 8, wherein the threaded bore of the proximal drive gear has a first thread pitch and the threaded bore of the distal drive gear has a second thread pitch that runs in a direction opposite the first thread pitch.

10. A steerable intravascular catheter as recited in claim 9, wherein a proximal end of one of the pull wires is anchored to the proximal drive sleeve and a proximal end of the other pull wire is anchored to the distal drive sleeve.

11. A steerable intravascular catheter as recited in claim 7, wherein the proximal end portion of the sheath extends entirely through the handle assembly and terminates at a sealed access port communicating with the central lumen defined by the tubular body.

* * * * *